(12) United States Patent
Dale et al.

(10) Patent No.: US 12,344,823 B2
(45) Date of Patent: Jul. 1, 2025

(54) METHOD FOR CONTINUOUS GROWTH OF FUNGAL MATERIAL

(71) Applicant: Mu Mycology, Hillsboro, OR (US)

(72) Inventors: Edward Dale, Hillsboro, OR (US); Natalie Dale, Hillsboro, OR (US); Nicolaas Vermeulen, Chicago, IL (US)

(73) Assignee: Mu Mycology, Hillsboro, OR (US)

( * ) Notice: Subject to any disclaimer, the term of this patent is extended or adjusted under 35 U.S.C. 154(b) by 0 days.

(21) Appl. No.: 18/672,722

(22) Filed: May 23, 2024

(65) Prior Publication Data

US 2024/0309303 A1    Sep. 19, 2024

Related U.S. Application Data

(62) Division of application No. 18/136,953, filed on Apr. 20, 2023, now Pat. No. 12,012,577.

(Continued)

(51) Int. Cl.
| | |
|---|---|
| *A01G 18/60* | (2018.01) |
| *A01G 18/62* | (2018.01) |
| *A01G 18/64* | (2018.01) |
| *A01G 18/69* | (2018.01) |
| *C12M 1/00* | (2006.01) |
| *C12M 1/12* | (2006.01) |

(Continued)

(52) U.S. Cl.
CPC .............. *C12M 1/16* (2013.01); *A01G 18/60* (2018.02); *A01G 18/62* (2018.02); *A01G 18/64* (2018.02); *A01G 18/69* (2018.02); *C12M 25/10* (2013.01); *C12M 25/14* (2013.01); *C12M 29/06* (2013.01); *C12M 41/12* (2013.01); *C12N 1/14* (2013.01)

(58) Field of Classification Search
CPC ........ A01G 18/60; A01G 18/62; A01G 18/64; A01G 18/69
USPC ........................................................... 47/1.1
See application file for complete search history.

(56) References Cited

U.S. PATENT DOCUMENTS

| | | |
|---|---|---|
| 2,618,900 A | 11/1952 | Humfeld |
| 2,928,210 A | 3/1960 | Cirillo |
| | (Continued) | |

FOREIGN PATENT DOCUMENTS

WO       2009007414 A1    1/2009

*Primary Examiner* — David J Parsley
(74) *Attorney, Agent, or Firm* — Bold IP PLLC; Binita Singh (57) ABSTRACT

A method using a system adapted for continuous growth and harvesting of fungal fruiting bodies. The system includes a growth chamber, one or more mycelium feed assemblies, a nutrient reservoir with liquid media, one or more environmental controls to control an environment within the growth chamber and of the liquid media within the nutrient reservoir. One or more mycelium feed assemblies are arranged within the growth chamber. Each of the one or more mycelium feed assemblies includes a nutrient supply member and a mycelium colony which grows around the nutrient supply member, that continuously supplies liquid media to the mycelium colony. The method includes starting one or more mycelium colonies on the nutrient supply member, establishing that a mature colony has formed, and then maintaining the mature mycelium colony by continuous delivery of liquid medium to the mycelium colony, thus allowing for contiguous generation and harvesting of fungal fruiting bodies.

20 Claims, 6 Drawing Sheets

Related U.S. Application Data (60) Provisional application No. 63/337,656, filed on May 3, 2022.

(51) Int. Cl.
  *C12M 1/16* (2006.01)
  *C12M 1/34* (2006.01)
  *C12N 1/14* (2006.01)

(56) References Cited

U.S. PATENT DOCUMENTS

| | | |
|---|---|---|
| 3,810,327 A | 5/1974 | Giansante |
| 4,226,047 A * | 10/1980 | Maaijwee ............... A01G 18/62 |
| | | 47/1.1 |
| 4,918,859 A | 4/1990 | Shevlin |
| 5,097,623 A | 3/1992 | Furuya et al. |
| 6,490,824 B1 * | 12/2002 | Maekawa ............... A01G 18/50 |
| | | 47/1.4 |
| 6,748,696 B1 | 6/2004 | Davidson |
| 10,426,107 B2 | 10/2019 | Jones et al. |
| 10,485,186 B2 | 11/2019 | Storey |
| 10,888,054 B2 | 1/2021 | Storey |
| 11,678,618 B1 | 6/2023 | Hrudka |
| 2011/0308148 A1 | 12/2011 | O'Connor |
| 2013/0199088 A1 | 8/2013 | Juscius |
| 2014/0000162 A1 | 1/2014 | Blank |
| 2015/0033620 A1 | 2/2015 | Greetham et al. |
| 2016/0073589 A1 | 3/2016 | McNamara et al. |
| 2019/0059431 A1 | 2/2019 | Kozubal |
| 2020/0344965 A1 | 11/2020 | Song et al. |
| 2021/0007304 A1 | 1/2021 | Kuhns |
| 2021/0037722 A1 | 2/2021 | Hall |
| 2021/0267142 A1 | 9/2021 | Ross |
| 2023/0217870 A1 | 7/2023 | Fox et al. |

* cited by examiner

Nutrient supply

Plurality of holes - Inline sterilization or pre-sterilized. Terminal or re-circulated.

FIG. 4A

Microporous - no sterilization needed. Terminal or re-circulated.

FIG. 4B

Injection - Inline sterilization or pre-sterilized. Terminal or re-circulated.

METHOD FOR CONTINUOUS GROWTH OF FUNGAL MATERIAL

CROSS-REFERENCE TO RELATED APPLICATIONS

This application is a divisional application which claim priority to the Non-Provisional patent application Ser. No. 18/136,953 filed on Apr. 20, 2023, which claims priority to U.S. Provisional Patent Application No. 63/337,656 filed on May 3, 2022, which are incorporated by reference in its entirety.

FIELD OF DISCLOSURE

The present disclosure relates generally to systems and methods for growing fungal materials, and in particular to a system and method of growing fungal materials for producing continuous flushes from a mycelium colony.

BACKGROUND

Mushrooms are a healthy addition to any diet and people enjoy mushrooms for their taste and/or health benefits. Mushrooms consist of two parts, mycelium and fruiting body. Mycelium is the vegetative part of the mushroom, which appears as white filaments that grow through a nutritious substrate. Mycelium may be thought of as the root structure of a mushroom. It is a vast, complex network of cells that form thin fibers, like plant roots, and spread under the forest floor in search of nutrients. Fruiting body is the part of the mushroom that can be harvested. This is typically the above-ground part of the mushroom, and the mycelium is the underground part of the mushroom.

Germination starts when a mushroom spore lands in a spot with ideal growing conditions and starts to produce thread-like filaments called hyphae that grow, interconnect, and form mycelium. Extensive networks of mycelium spread over large distances underground and connect fungi to each other. Mushrooms are different from plants as they do not have chlorophyll like plants for food production. Instead, the mycelium grows by absorbing nutrients from dead and decaying organic matter. The fruiting body usually grows above the ground or on the surface of the host. The mycelium may be considered the main part of the mushroom and it is vital for the growth of the entire mushroom as the mycelium absorbs nutrients for the mushroom and produces fruiting bodies.

Conventional gourmet mushroom growth uses liquid culture starters and a solid nutrient source (e.g., compost, wood chips, grains) to generate a few flushes before needing to be recycled and the process started from scratch. This is a conventional farming technique, and it scales from small to large scale operations. Fruiting mushrooms require the use of a solid growth medium, but the mushrooms can also be grown to fruit without the solid and non-replenishable medium. Liquid media have been used to grow mushrooms, but these techniques require the use of large reactors and preclude the ability of the mushrooms to make fruiting bodies.

Accordingly, there exists a need for growing mushrooms using a liquid medium as the nutrient source specifically designed to allow the mushrooms to flush and make fruiting bodies on a continuous fruiting cycle. This will significantly impact the growth rate and fruiting cycles (flushes) as compared to conventionally grown mushrooms.

SUMMARY

The present description relates to a novel and unique cultivation system that allows for continuous growth and harvest of fungal fruiting bodies-mushrooms. As the fruiting bodies can be harvested for food and nutrition, a fungal colony is replenished with nutrients and allowed to fruit in a continuous fashion.

In one or more non-limiting embodiment, a system for a continuous growth and harvesting of fungal fruiting bodies is disclosed to comprise of a growth chamber, one or more mycelium feed assemblies, a nutrient reservoir with liquid media, and one or more environmental controls to control the environment within the growth chamber and of the liquid media within the nutrient reservoir. The growth chamber is an enclosed system to help maintain a sterile environment within the growth chamber. The one or more mycelium feed assemblies are arranged within the growth chamber. Each of the one or more mycelium feed assemblies includes a nutrient supply member and a mycelium colony which grows around the nutrient supply member. The nutrient supply member has a hollow tubular structure and may further include a media diffusing portion which includes a plurality of holes or includes micropores. A nutrient supply line connects the nutrient reservoir to the mycelium feed assemblies to continuously supply liquid media to the mycelium colony through the media diffusing portion. The liquid media can be returned to the nutrient reservoir to replenish the liquid media with nutrients, or the liquid media is not returned, and fresh media is supplied to the system.

In one or more non-limiting embodiments, a method for continuous growth and harvesting fungal fruiting bodies is disclosed. The method includes providing a system for the continuous growth and harvesting of fungal fruiting bodies, as described above. The method further includes starting one or more mycelium colonies, from progenitors, to grow on the nutrient supply member. The method further includes establishing that a mature colony has formed and then maintaining the mature mycelium colony by connecting the nutrient reservoir to the one or more mycelium feed assemblies to continuously deliver liquid medium to the mycelium colony. Whereby, continuous delivery of the liquid media to the mycelium colony allows for continuous growth of the mycelium and allows for continuous generation and harvesting of fungal fruiting bodies.

Other aspects and advantages of the invention will be apparent from the following description and the appended claims.

BRIEF DESCRIPTION OF THE FIGURES

The present invention will be described by way of exemplary embodiments, but not limitations, illustrated in the accompanying drawings in which like references denote similar elements, and in which.

DETAILED DESCRIPTION

In the Summary above and in this Detailed Description, and the claims below, and in the accompanying drawings, reference is made to particular features of the invention. It is to be understood that the disclosure of the invention in this specification includes all possible combinations of such particular features. For example, where a particular feature is disclosed in the context of a particular aspect or embodiment of the invention, or a particular claim, that feature may also be used, to the extent possible, in combination with and/or in the context of other particular aspects and embodiments of the invention, and in the invention generally.

Where reference is made herein to a method comprising two or more defined steps, the defined steps may be carried out in any order or simultaneously (except where the context excludes that possibility), and the method may include one or more other steps which are carried out before any of the defined steps, between two of the defined steps, or after all the defined steps (except where the context excludes that possibility).

"Exemplary" is used herein to mean "serving as an example, instance, or illustration." Any aspect described in this document as "exemplary" is not necessarily to be construed as preferred or advantageous over other aspects.

Throughout the drawings, like reference characters are used to designate like elements. As used herein, the term "coupled" or "coupling" may indicate a connection. The connection may be a direct or an indirect connection between one or more items. Further, the term "set" as used herein may denote one or more of any item(s), so a "set of items" may indicate the presence of only one item or may indicate more items. Thus, the term "set" may be equivalent to "one or more" as used herein.

The present disclosure recognizes the unsolved need for extending the number of fruiting cycles of a mycelium. The present disclosure provides for a system that allows mushrooms to flush and make fruiting bodies on a continuous cycle. The present disclosure also provides for a method to grow a mycelium colony that is fed by a nutritious liquid source indefinitely to continuously flush and make fruiting bodies.

As used herein, the term "immature colony" refers to mycelium that requires a scaffold and/or a nutrient rich solid medium that may be transitioned to a mature colony. The term "mature colony" refers to a self-standing mycelium colony that may have a scaffold and is fed by a nutritious liquid medium source indefinitely. The term "scaffold" refers to a solid support for a mycelium colony which may include nutritious or non-nutritious support. The term "nutritious liquid media" refers to carbohydrate-rich fluid, which may or may not include additional supplementation. The term "fruiting bodies" refers to the part of the mushroom that can be harvested. The term "fruiting" refers to the production of fruiting bodies of the mushroom, and in particular refers to the continuous fruiting which should occur as long as the nutrient rich liquid media remains available to the mycelium colony. The term "feeding" refers to supplying a nutritious liquid media to the mycelium colony.

The present disclosure includes a system and method for continuous growth and harvesting of fungal fruiting bodies. The system and method use a continuous supply of nutrient rich liquid media to a mature mycelium colony. The system that is adapted to allow continuous growth and harvesting of fungal fruiting bodies is focused on a continuous delivery of nutrient rich liquid media to the mycelium for continuous growth and harvest. The method of continuous fruiting may be initiated in two stages. The first stage may be the process of starting and establishing the immature colony. This stage is the process of starting to grow mycelium from a mushroom progenitor. The second stage involves transitioning to and maintaining a mature colony of mycelium. This stage requires a continuous supply of nutrient rich media to generate fruiting bodies continuously or at regular intervals. The liquid media provides nutrients for the mycelium, which in turn produces fruiting bodies (mushrooms). The mushrooms are harvested and, since the mycelium continues to receive liquid nutrients, the cycle begins again, allowing for continuous, cyclical harvest.

The presently disclosed system, that is adapted to allow continuous growth and harvesting of fungal fruiting bodies, is a liquid media delivery system that uses liquid medium to grow mushrooms to fruiting bodies without the use of solid medium. In this system, the mushrooms can be grown to fruiting on a continuous cycle using a nutritious liquid growth medium which is being continuously pumped through the system. The continuous mushroom cultivation system may comprise of a growth chamber, a nutrient reservoir, a nutrient delivery system, a mycelium feed assembly, and one or more environmental control features. The growth chamber may be an enclosed chamber within which the mycelium feed assembly is arranged to grow an immature colony to a mature colony and allow the mushrooms to fruit on a continuous cycle. The nutrient reservoir may store liquid media and supplies nutrients to the mycelium colony in the growth chamber through the nutrient delivery system. The environmental control features may control the environment within the growth chamber and may also include environmental control of the liquid media. The mycelium colony will grow around or on the mycelium feed assembly and produce fruiting bodies, which can be harvested, and fruiting may continue as long as there is access to the nutritious liquid providing continuous flushes.

Figure 1:
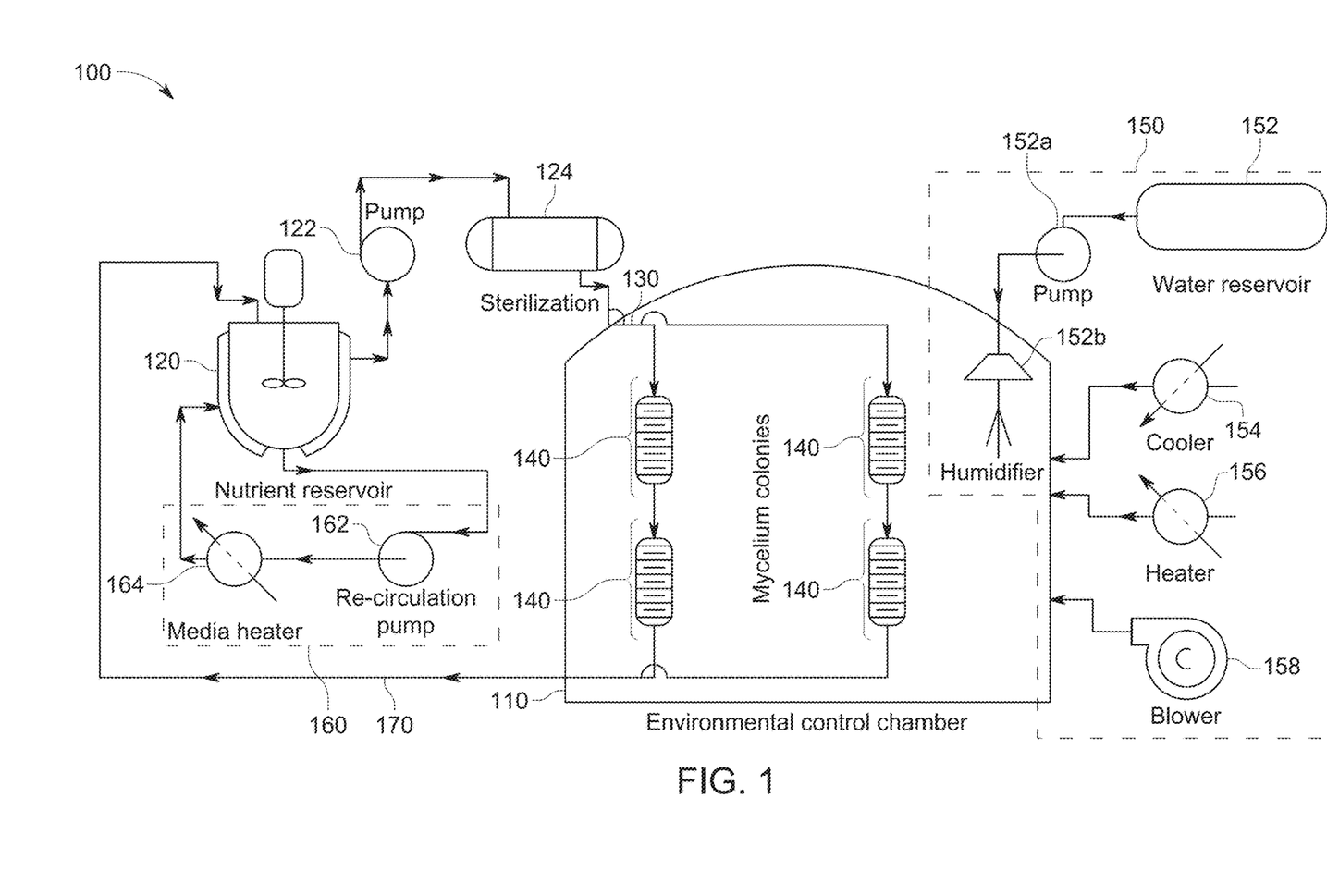
FIG. 1 shows an example embodiment of a system adapted for growing mushrooms to flush and make fruiting bodies on a continuous cycle.
Figure 2:
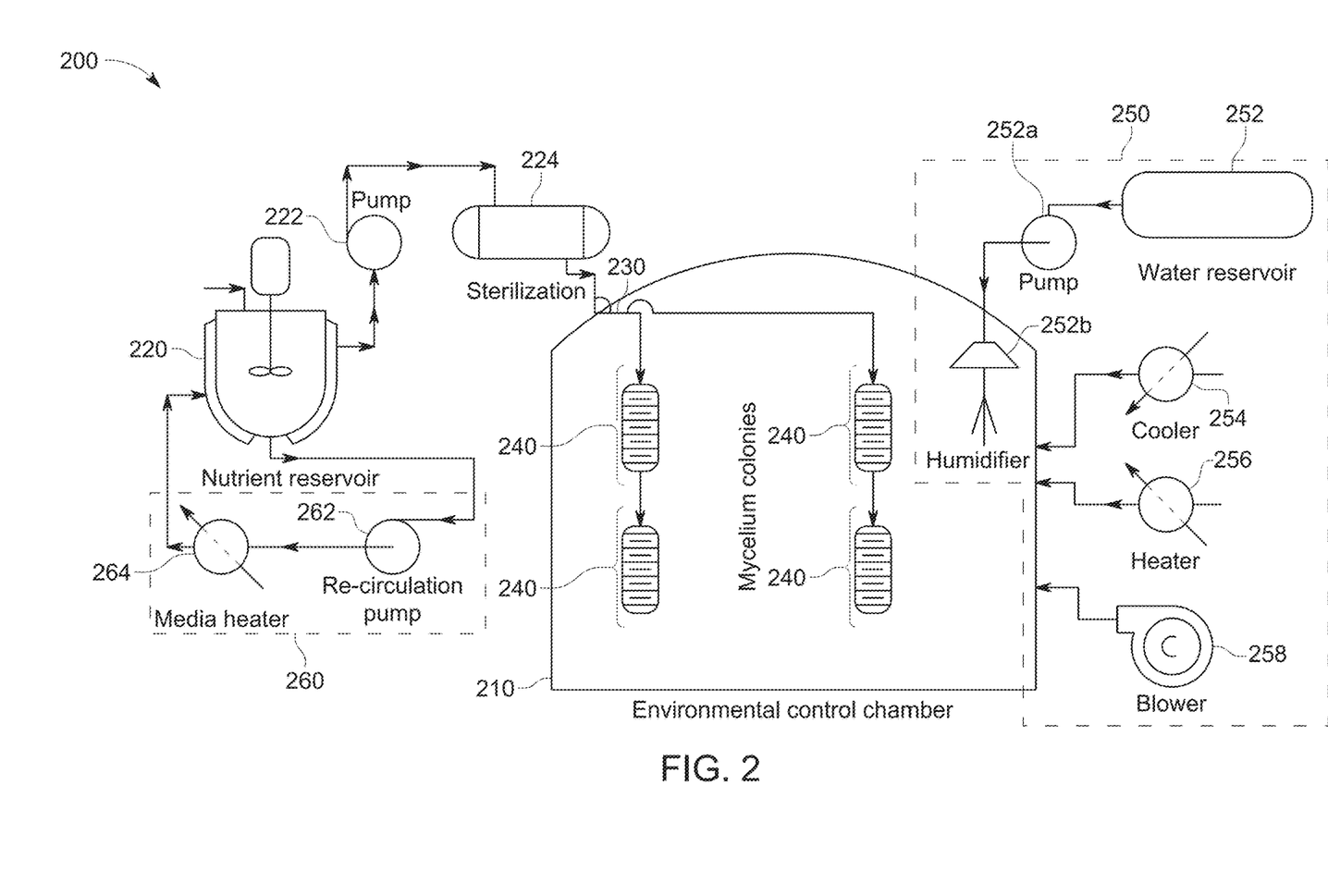
FIG. 2 shows an alternate example embodiment of a system adapted for growing mushrooms to flush and make fruiting bodies on a continuous cycle.

The presently disclosed liquid media delivery system adapted to allow continuous growth and harvesting of fungal fruiting bodies is more fully described in conjunction with the figures. Referring to FIGS. 1 and 2, two example embodiments of a liquid media delivery system are illustrated as showing a continuous-loop system 100 and a non-continuous system 200. FIG. 1 illustrates the continuous-loop liquid media delivery system 100 comprising of a growth chamber 110, a nutrient reservoir 120, a nutrient supply line 130, a mycelium feed assembly 140, one or more growth chamber environmental control elements 150, one or more liquid media environmental control elements 160, and a recirculation line 170. The liquid media is contained within the nutrient reservoir 120 and the used media diffused through the mycelium feed assembly 140 is circulated back into the nutrient reservoir 120. FIG. 2 illustrates the non-continuous liquid media delivery system 200 which comprises of a growth chamber 210, a nutrient reservoir 220, a nutrient supply line 230, a mycelium feed assembly 240, one or more growth chamber environmental control elements 250, and one or more liquid media environmental control elements 260. In this example embodiment, the liquid media circulated from the nutrient reservoir 220 is not circulated back after it has been delivered to the mycelium feed assembly 240, or in other words the liquid medium terminates in the mycelium feed colony and does not recirculate.

Both the systems 100, 200 focus on supplying a nutrient rich liquid medium contained within the nutrient reservoir 120, 220 to a mature colony of mycelium on the mycelium feed assembly 140, 240 in the growth chamber 110, 210, respectively. In one embodiment, the liquid medium may contain carbohydrates and a mixture of nitrogen, phosphorous, carbon, and metal sources. The carbohydrate source may be used in the initial immature growth media (discussed later in FIG. 4) and may be a major source of all nutrients for a mature colony on the mycelium feed assembly 140, 240. It is to be understood that the liquid medium may contain carbohydrates and may not include additional supplementation. As the mature colony(ies) on the mycelium feed assembly 140, 240 are continuously replenished with the liquid medium, the mature colony(ies) will be able to generate fruiting bodies continuously or at regular intervals until the nutrient flow is stopped. Fruiting may also be controlled or promoted, in each of the systems 100, 200, by controlling the one or more growth chamber environmental control elements 150, 250, respectively. It is also to be understood that the liquid medium may be tailored to a specific colony 140, 240 if there are multiple colonies growing in the growth chamber or may also be tailored to a specific growth cycle during multiple flushes.

FIG. 1 illustrates additional components comprising the continuous-loop liquid media delivery system 100 that may promote the mycelium colony on the mycelium feed assembly 140 to continuously fruit. As mentioned above, the mycelium feed assembly 140 is continuously supplied with the nutritious liquid media which is contained within the nutrient reservoir 120. The nutrient reservoir 120 may be connected to a pump 122 which pumps the liquid media to the mycelium feed assembly 140. The pump 122 may first pump the liquid media to a sterilization tank 124 from the nutrient reservoir 120. The sterilized liquid media may then be delivered to the mycelium feed assembly 140 through the nutrient supply line 130 connected to the sterilization tank 124. It is to be understood that if the liquid media is directly delivered to the mycelium feed assembly 140 from the nutrient reservoir 120, then the nutrient supply line 130 will be connected to the pump 122. In this example embodiment of the continuous-loop liquid media delivery system 100, the liquid media delivered to the mycelium feed assembly 140 is recirculated back to the nutrient reservoir 120 which may be replenished with the key nutrients and continued through the pump 122 and the sterilization tank 124 to the mycelium feed assembly 140 in the growth chamber 110.

The liquid nutrient media may be pumped into the mycelium feed assembly 140 through a pump connected to the nutrient supply line 130, shown in FIG. 1. In an alternative embodiment, the sterilized liquid media (either in the nutrient reservoir 120 or the sterilization tank 124 in FIG. 1) may be suspended above the mycelium feed assembly 140 and function with gravity providing liquid pressure to deliver liquid media to the mycelium feed assembly 140. Additionally, another alternate delivery method may include a capillary action which is where the liquid media would flow in a narrow space (e.g., a nutrient supply member 142 in FIGS. 3, 4A, and 4B) without the assistance of any external forces. In these delivery methods, the flow rate and the pressure of the liquid medium may be monitored and controlled via valves, flow restrictors, and a diameter of a tubing (see, porous tube 142 in FIGS. 3 and 4A to 4C) comprising part of the mycelium feed assembly 140, or any other system that would allow for control of liquid flow rate and pressure.

Figure 3:
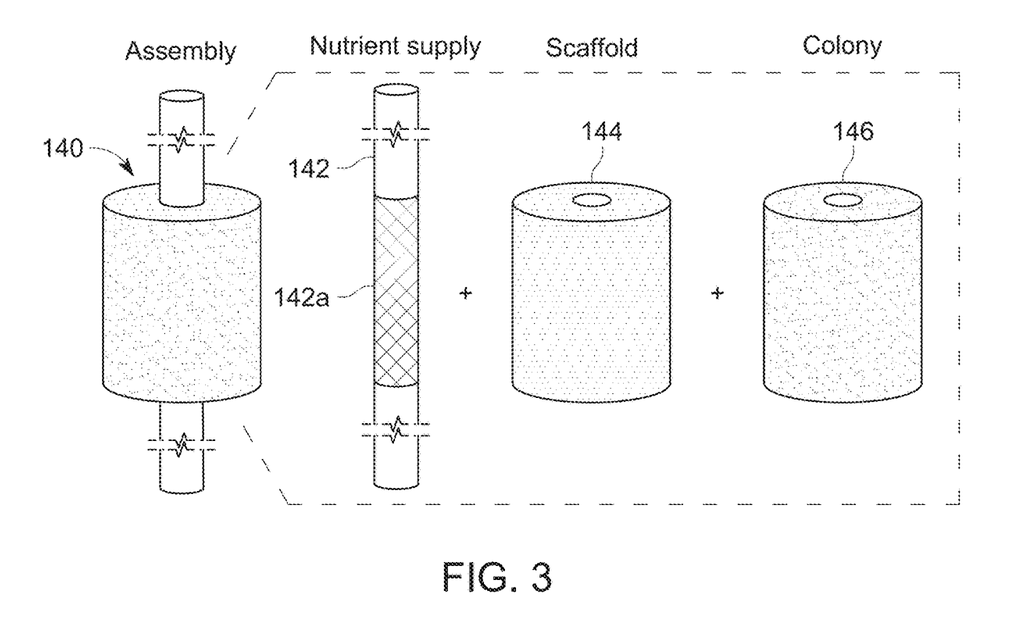
FIG. 3 shows an example mycelium feed assembly according to one or more embodiments.

Referring to FIGS. 3 and 4A to 4C, the mycelium feed assembly 140 is illustrated in more detail. The mycelium feed assembly 140 may comprise of a nutrient supply member 142 and a scaffold 144. FIG. 3 also illustrates a mycelium colony 146 which may colonize throughout the scaffold 144. As defined above, the scaffold 144 provides a solid support for a mycelium progenitor to grow a mycelium colony (discussed below). The scaffold 144 is placed around or formed around the nutrient supply member 142 so that the liquid media can diffuse through the nutrient supply member 142 to the scaffold 144 and the growing mycelium colony 146. Once the mycelium colony 146 has matured, the scaffold 144 may remain or the scaffold is consumed, but the shape and structure of the mycelium colony 146 remains and continues to grow around the nutrient supply member 142 to yield fruiting bodies that may be harvested.

Figure 4A:
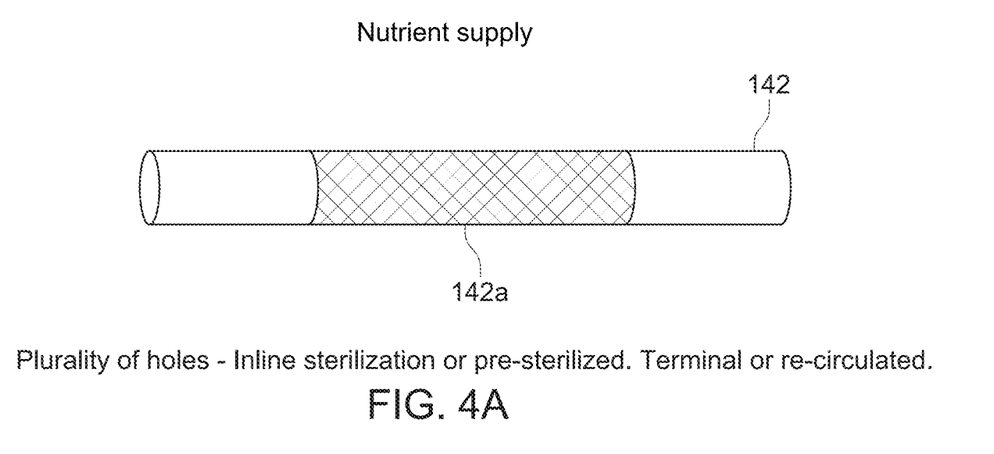
FIG. 4A-4C show one or more examples of mycelium nutrient supply which may comprise part of a mycelium feed assembly.
Figure 4B:
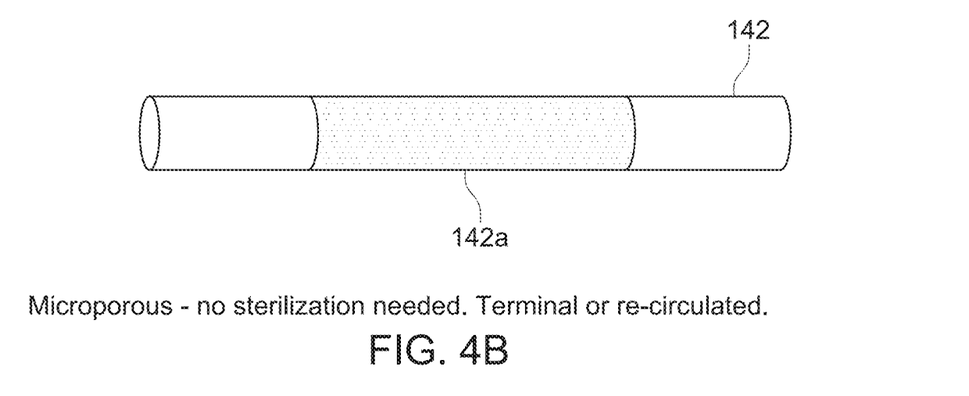
Figure 4C:
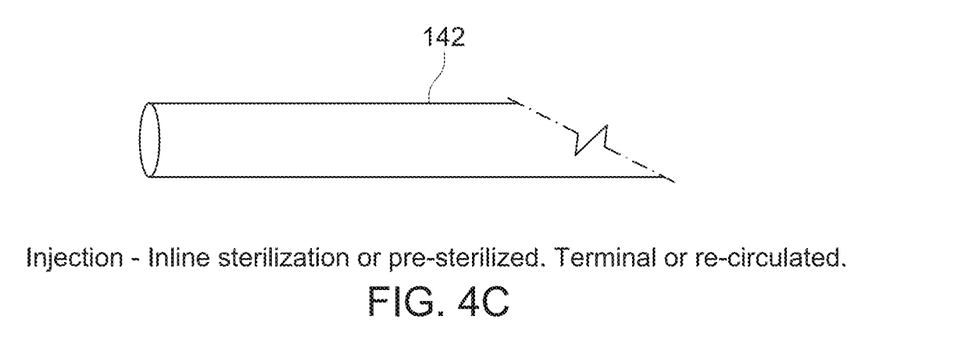

FIG. 3 illustrates that the nutrient supply member 142 is a hollow tubular structure and may include a media diffusing portion 142a. The liquid media being delivered through the nutrient supply member 142 will diffuse through the media diffusing portion 142a and into the mycelium colony 146. FIGS. 4A and 4B illustrate the nutrient supply member 142 with two examples of media diffusing portions 142a. In FIG. 4A, the media diffusing portion 142a of nutrient supply member 142 may comprise of a plurality of holes. FIG. 4B illustrates that the media diffusing portion 142a may comprise of micropores. In both non-limiting examples, the liquid media diffuses through the media diffusing portions 142a to feed the mycelium colony (146 in FIG. 3). The nutrient supply members shown in FIGS. 4A and 4B may be considered as a multipoint feeding system wherein the liquid media is fed through the nutrient supply member 142 located inside the mycelium colony 146. Capillary action in FIG. 4C shows an alternative nutrient supply member 142 which may be like a needle inserted into a mycelium colony 146. In this supply method, the liquid media may slowly diffuse into the mycelium colony through the needle like nutrient supply member (similar to an intravenous drip system). In all three systems, the nutrient supply member 142 may penetrate through the mycelium colony 146 to allow for recirculation of the media as in the continuous-loop liquid media delivery system 100 of FIG. 1. Alternatively, in all three systems, the nutrient supply member 142 may terminate in the mycelium colony 146 as shown in the non-continuous liquid media delivery system 200 of FIG. 2.

Additionally, there may be several types of connections possible to deliver the liquid media to the mycelium colony 146. One such example may include the connection between the reservoir to the mycelium feed assembly 140, which may refer to the nutrient supply line 130. Then, there may be connections between the mycelium feed assembly 140 to another mycelium feed assembly 140, wherein the assemblies may be arranged in line and the mycelium feed assemblies are connected through the nutrient supply member 142, allowing the liquid media to move through each and diffuse into the mycelium colony 146. Another connection is the mycelium feed assembly 140 is connected back to the reservoir to circulate the liquid, which may refer to the recirculation line 170 (FIG. 1). In the alternate, the mycelium feed assembly 140 may be connected to a waste component, wherein the liquid media is not recirculated (FIG. 2 is an example of the non-circulating system).

The continuous-loop liquid media delivery system 100 also comprises of the one or more growth chamber environmental control elements 150 and one or more liquid media environmental control elements 160. The environmental controls 150, 160 allow an environment within the growth chamber 110 and the liquid media to be controlled. There may be several environmental variables that can be controlled and monitored. Some examples of the growth chamber environmental controls may include, and not be limited to, temperature, humidity, light, atmosphere, gas composition, air flow, and turn over volume. FIG. 1 illustrates some examples, such as humidity control which may include a water reservoir 152, a humidifier 152*b*, and a pump 152*a* connected to the water reservoir 152 and the humidifier 152*b*. Also shown is a cooler 154, a heater 156, and a blower 158, wherein all are connected to the growth chamber 110 and controlling their specific environmental variable within the growth chamber 110. Environmental control of the liquid media may include and not be limited to temperature of the media, which is shown in FIG. 1 with a media heater 164. A recirculation pump 162 is connected to the nutrient reservoir 120 which pumps media to the media heater 164 which gets returned to the nutrient reservoir and the cycle continues to maintain the temperature of the liquid media.

FIG. 2 illustrates the noncontinuous loop liquid media delivery system 200, which is similar to the system of FIG. 1, with the exception that FIG. 2 depicts that the media from the mycelium feed assembly 240 does not get recirculated back to the nutrient reservoir 220. To note, FIG. 2 also illustrates additional components comprising the noncontinuous-loop liquid media delivery system 200 that may promote the mycelium colony on the mycelium feed assembly 240 to continuously fruit. The mycelium feed assembly 240 is also continuously supplied with the nutritious liquid media, which is contained within the nutrient reservoir 220, but is not circulated back to the nutrient reservoir 220. The nutrient reservoir 220 may be connected to a pump 222 which pumps the liquid media to the mycelium feed assembly 240. The pump 222 may first pump the liquid media to a sterilization tank 224 from the nutrient reservoir 220. The sterilized liquid media may then be delivered to the mycelium feed assembly 240 through the nutrient supply line 230 connected to the sterilization tank 224. If the liquid media is directly delivered to the mycelium feed assembly 240 from the nutrient reservoir 220, then the nutrient supply line 230 will be connected to the pump 222. In this example embodiment of the noncontinuous-loop liquid media delivery system 200, the liquid media delivered to the mycelium feed assembly 240 is not recirculated back to the nutrient reservoir 220 but is delivered to a waste component.

The noncontinuous-loop liquid media delivery system 200 also comprises of the one or more growth chamber environmental control elements 250 and one or more liquid media environmental control elements 260 allowing an environment within the growth chamber 210 and the liquid media to be controlled. Like the embodiment in FIG. 1, there may be several environmental variables that can be controlled and monitored, such as humidity which may include a water reservoir 252, a humidifier 252*b*, and a pump 252*a* connected to the water reservoir 252 and the humidifier 252*b*. Also shown is a cooler 254, a heater 256, and a blower 258 to control their specific environmental variable within the growth chamber 210. FIG. 2 also shows the environmental control of the liquid media may include and not be limited to temperature of the media with a media heater 264 and a recirculation pump 262.

The presently disclosed method for generating fruiting bodies continuously or at regular intervals are more fully described in conjunction with the figures.

Figure 5:
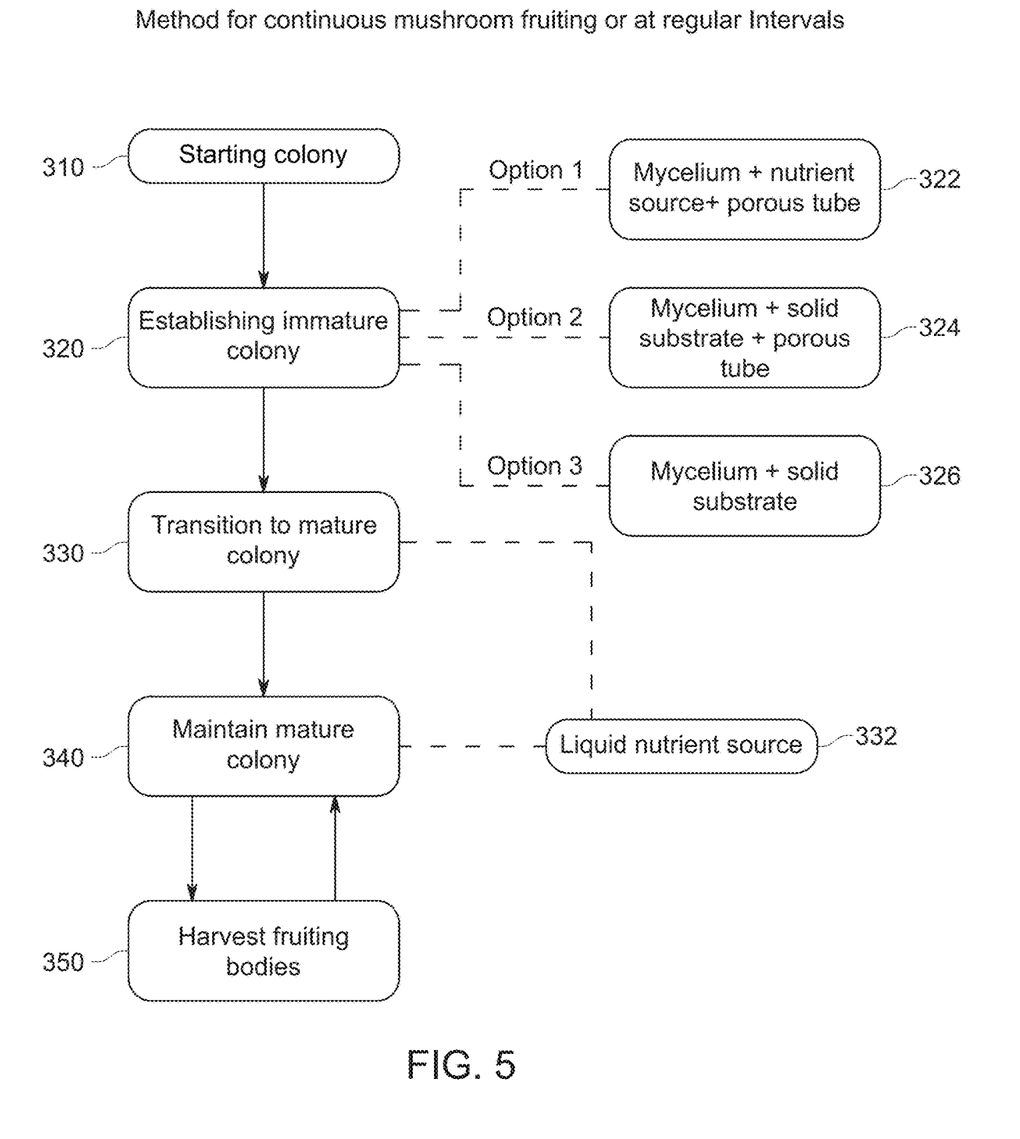
FIG. 5 shows example steps of a method of growing mushrooms and producing fruiting bodies on a continuous or a regular cycle according to one or more embodiments.

In some embodiments as shown in FIG. 5, a method of continuous fruiting is shown that may be initiated in two stages. The first stage may be the process of starting and establishing the immature colony. The second stage involves transitioning to and maintaining a mature colony of mycelium. This stage requires a continuous supply of nutrient rich media to generate fruiting bodies continuously or at regular intervals.

Figure 6:
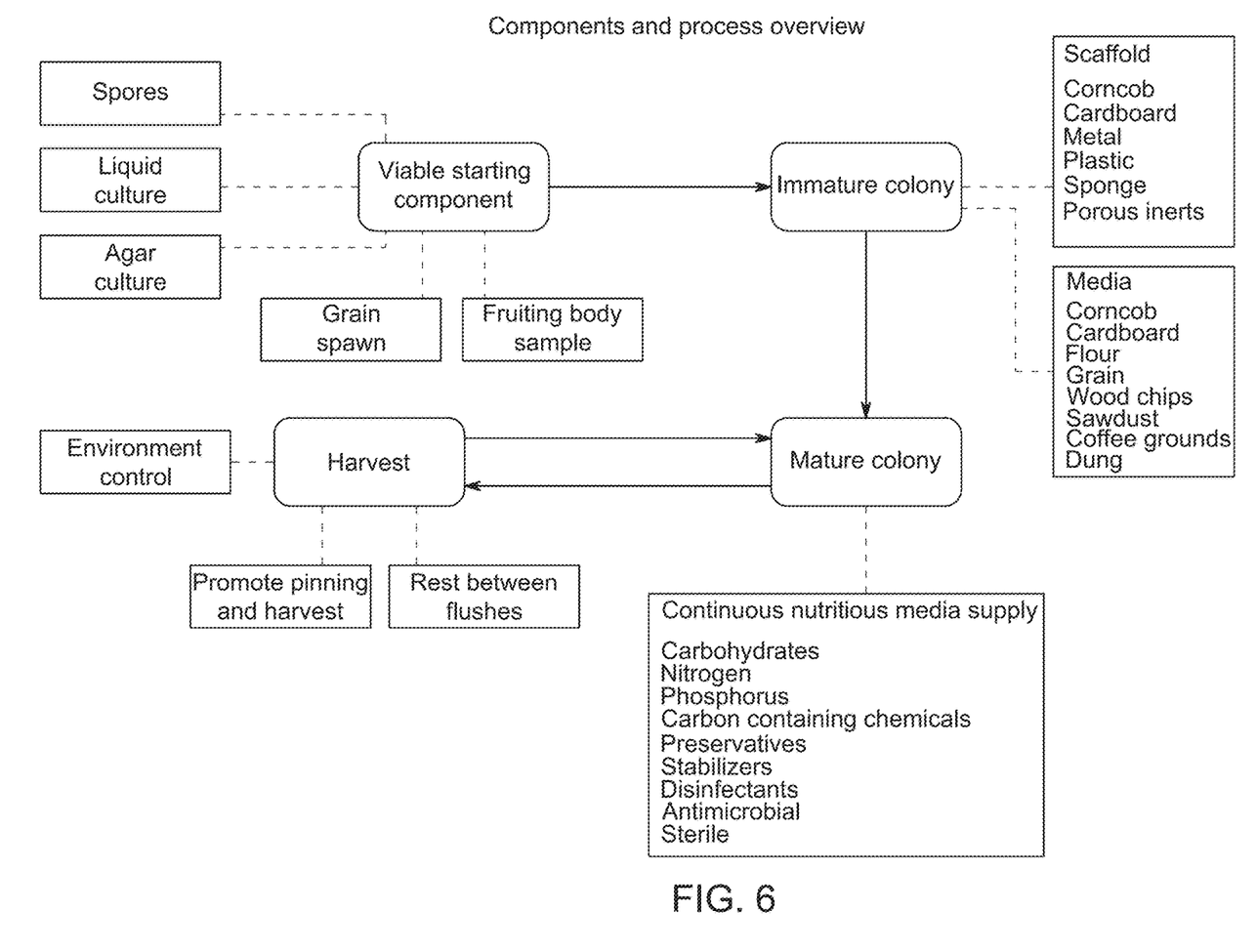
FIG. 6 shows an example of components that may be used at various steps in the process of growing mushrooms and producing fruiting bodies on a continuous or a regular cycle according to one or more embodiments.

In the first step (at 310), a mycelium colony is started. In this step, a viable mushroom progenitor may be used to start the process of growing mycelium. The initial mycelium may be incubated from several components. FIG. 6 illustrates the process and the components at some of the key steps. As depicted, the viable starting components may include and not be limited to mushroom spores, liquid culture, agar culture, grain spawn, or fruiting body sample. The process of starting a colony is well known in the arts and may be used in this step.

In the next step (at 320), an immature colony is established. This is established by using the mushroom progenitor from step 310 to grow a mycelium colony on a nutritious solid growth medium. This step requires a clean, sterile environment as the nutrient source may be susceptible to infection from bacterial, yeasts, other fungi, or a variety of competitive organisms. FIG. 6 illustrates several nutrient sources using a scaffold or media that may be used to establish the immature colony. Thus, this step requires a controlled environment to ensure mycelial growth.

One or more options may be available to establish an immature colony from a mushroom progenitor. FIG. 5 also illustrates examples of these options to start establishing the immature colony. Option 1 (in step 322) uses mycelium mixed with a nutrient source and formed around a nutrient supply member (see, nutrient supply member 142 in FIG. 3) without a scaffold (or a solid support). This requires a putty like media to keep a shape of the mycelium colony until the mycelium colony is mature.

Option 2 (in step 324) uses mycelium with solid nutrient around the nutrient supply member (see, nutrient supply member 142 in FIG. 3) with a scaffold. This option allows for a less structural media to be used. The scaffold can be chosen from a list consisting of corncob, cardboard, metal, plastic, sponge, or porous inert material.

Option 3 (in step 326) uses mycelium with a solid nutrient formed without the nutrient supply member. This may or may not use a solid support which would grow into a mature colony. At some point, the nutrient supply member (see, nutrient supply member 142 in FIG. 3) may need to be inserted into or through the growing and maturing mycelium colony (see, mycelium colony 146 in FIG. 3).

In any of these options, the nutrient supply member 142 (see, FIG. 3) may go all the way through the mycelium colony 146 (see, FIG. 3) which may allow for the liquid media to circulate through as in FIG. 1 and FIG. 2. Alternatively, the nutrient supply member 142 may go partway through the mycelium colony allowing for the use of a non-circulating liquid medium described above in FIG. 4C which may be like a needle inserted into a mycelium colony 146. In this supply method, the liquid media may slowly diffuse into the mycelium colony through the needle like nutrient supply member (similar to an intravenous drip system). The mycelium colony can be formed or molded to any shape or loosely held together.

Next (in step 330), the growing mycelium colony can be transitioned to a mature colony. If the nutritious scaffold, or the nutrients have been consumed, then the immature colony from step 320 may be considered a mature colony. Transitioning to a mature colony in step 330 requires that the mycelium colony will need a supply of nutrient rich liquid medium (shown in step 332), because the nutrient source from step 320 is depleted or not available. The mature colony is transitioned to a liquid media, which contains carbohydrates and may contain other nutrients such as a mixture of nitrogen, phosphorous, carbon, and metal sources, as detailed in FIG. 6. The carbohydrate source may be a major source of all the nutrients for the colony and may comprise of simple sugar, or complex oligomers and polymers, or both. The liquid medium source may also contain preservatives, stabilizers, disinfectant, and/or antimicrobials. Additionally, the liquid media may be sterile or require sterilization before being fed to the mature mycelium colony. As discussed above in FIG. 1, a sterilization tank 124 may be connected to the nutrient reservoir 120.

In the next step (at 340), the mature colony is maintained and continuously replenished with the liquid nutrient source from step 332. This ensures that the mycelium colony is supplied with a nutritious liquid media that promotes fruiting.

In the last step (at 350), the fruiting bodies may be harvested. The mushrooms fruit from the mature mycelium colony as the nutrient rich liquid is continuously circulated through the system 100, 200 (See, FIGS. 1 and 2, respectively) and thus, as the fruiting bodies are harvested, the mycelium colony can continue to make more fruiting bodies as the liquid nutrient source is maintained and circulated through.

Steps 340 and 350 are repeated whereby the resulting product is that fruiting may continue as long as there is access to the nutritious liquid media.

Thus, the system described herein is a novel system in that it allows for continuous cycles of growth and harvest from an established colony. Due to the use of a nutrient rich liquid media source to maintain a mycelium colony, the system can produce numerous flushes without creating the volume of waste of traditional substrates. The next cycle can begin immediately after harvest, circumventing the inoculation and colonization phases entirely. Once the system is in place, using a preestablished colony, growers can expect to harvest about every 2 weeks. The system described herein is also a very sustainable system. The mycelial cake is reused-acting as a scaffold for a continuous mycelial colony rather than a sacrificial nutrient source—and the liquid media recycled, so the whole system produces very little waste. In comparison to a traditional approach, using a pre-formulated nutritious media, all mass will be converted into mushroom mass, leading to much higher biological efficiencies with respect to the starting scaffold material.

It is understood that the acts described above are meant as a general overview and demonstration of an exemplary method, and that the method may include different and/or additional acts as described herein or otherwise. While the present system has been described as having particular configurations disclosed herein, the present system can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description but is not intended to be exhaustive or limited to the invention in the form disclosed. Many modifications and variations will be apparent to those of ordinary skill in the art without departing from the scope and spirit of the invention. The embodiments were chosen and described in order to best explain the principles of the invention and the practical application, and to enable others of ordinary skill in the art to understand the invention for various embodiments with various modifications as are suited to the particular use contemplated. The present invention according to one or more embodiments described in the present description may be practiced with modification and alteration within the spirit and scope of the appended claims. Thus, the description is to be regarded as illustrative instead of restrictive of the present invention.

What may be claimed is:

1. A method for continuous growth and harvesting of fungal fruiting bodies, comprising:
    providing a system for the continuous growth and harvesting of fungal fruiting bodies, the system comprising:
        a growth chamber, wherein the growth chamber is an enclosed system to maintain a sterile environment;
        one or more mycelium feed assemblies arranged within the growth chamber, wherein each of the one or more mycelium feed assemblies includes a nutrient supply member having a hollow tubular structure; and
        a nutrient reservoir containing liquid media;
    starting one or more mycelium colonies on the one or more mycelium feed assemblies using mushroom progenitors and a scaffold, wherein the mushroom progenitors are mixed with the scaffold and formed around the nutrient supply member;
    establishing that an immature mycelium colony has transitioned to a mature mycelium colony by determining whether the one or more mycelium colonies have started growing around the nutrient supply member after consuming the scaffold or if the scaffold is not nutritious;
    maintaining the mature mycelium colony by connecting the nutrient reservoir to the one or more mycelium feed assemblies whereby the liquid media is continuously delivered to the mature mycelium colony for continuous growth and generation of fungal fruiting bodies;
    harvesting the fungal fruiting bodies; and
    continuing the supply of the liquid media to the mature mycelium colony to maintain a continuous cycle of growth and harvesting of fungal fruiting bodies of the mature mycelium colony.

2. The method of claim 1, wherein a method of starting the one or more mycelium colonies is chosen from the following:
    mixing the mushroom progenitors with a putty like scaffold and forming around the nutrient supply member;
    mixing the mushroom progenitors with a solid scaffold and forming around the nutrient supply member; or
    mixing the mushroom progenitors with a solid scaffold without the nutrient supply member, wherein the mushroom progenitors transition to a mature colony, and the nutrient supply member is inserted into the mature colony.

3. The method of claim 2, wherein the putty like scaffold comprises corncob, cardboard, flour, grain, wood chips, sawdust, coffee grounds, or dung.

4. The method of claim 2, wherein the solid scaffold comprises corncob, cardboard, metal, plastic, sponge, or porous inert material.

5. The method of claim 1, further comprising, diffusing the liquid media to the mature mycelium colony, wherein the nutrient supply member has a media diffusing portion, wherein the liquid media delivered through a connected nutrient supply line diffuses through the media diffusing portion to the mature mycelium colony growing on the nutrient supply member, wherein:
the media diffusing portion includes a plurality of holes or micropores.

6. The method of claim 1, further comprising, recirculating the liquid media from the nutrient supply member, with the mature mycelium colony, to the nutrient reservoir to replenish the liquid media with nutrients, wherein a recirculation line connects the nutrient supply member and the nutrient reservoir.

7. The method of claim 1, wherein nutrients in the liquid media comprises carbohydrates.

8. The method of claim 1, further comprising, sterilizing the liquid media in a sterilization tank, connected to the nutrient reservoir, prior to delivering the liquid media to the one or more mycelium feed assemblies.

9. The method of claim 1, further comprising, controlling an environment within the growth chamber by adjusting one or more growth chamber environmental controls, including temperature, humidity, light, gas compositions, and air flow.

10. A method for continuous growth and harvesting of fungal fruiting bodies, comprising:
providing a system for the continuous growth and harvesting of fungal fruiting bodies comprising one or more mycelium feed assemblies and a nutrient reservoir, wherein each of the one or more mycelium feed assemblies includes a nutrient supply member;
starting one or more mycelium colonies on the one or more mycelium feed assemblies using mushroom progenitors and a scaffold, wherein the mushroom progenitors are mixed with the scaffold and formed around the nutrient supply member;
establishing that an immature mycelium colony has transitioned to a mature mycelium colony by determining whether the one or more mycelium colonies continue growing on the one or more mycelium feed assemblies after the scaffold is consumed or if the scaffold is not nutritious;
maintaining the mature mycelium colony by connecting the nutrient reservoir to the one or more mycelium feed assemblies to continuously deliver a liquid media to the mature mycelium colony;
harvesting the fungal fruiting bodies forming in the mature mycelium colony; and
continuing the supply of the liquid media to the mature mycelium colony to maintain a continuous cycle of growth and harvesting of fungal fruiting bodies of the mature mycelium colony.

11. The method of claim 10, wherein a method of starting the one or more mycelium colonies is chosen from the following:
mixing the mushroom progenitors with a putty like scaffold and forming around the nutrient supply member;
mixing the mushroom progenitors with a solid scaffold and forming around the nutrient supply member; or
mixing the mushroom progenitors with a solid scaffold without the nutrient supply member, wherein the mushroom progenitors transition to a mature colony, and the nutrient supply member is inserted into the mature colony.

12. The method of claim 11, wherein the putty like scaffold comprises corncob, cardboard, flour, grain, wood chips, sawdust, coffee grounds, or dung.

13. The method of claim 11, wherein the solid scaffold comprises corncob, cardboard, metal, plastic, sponge, or porous inert material.

14. The method of claim 10, further comprising, diffusing the liquid media to the mature mycelium colony, wherein each of the one or more mycelium feed assemblies has a media diffusing portion, wherein the liquid media delivered through a connected nutrient supply line diffuses through the media diffusing portion to the growing mature mycelium colony, wherein:
the media diffusing portion includes a plurality of holes or micropores.

15. The method of claim 10, further comprising, recirculating the liquid media from the nutrient supply member, with the mature mycelium colony, to the nutrient reservoir to replenish the liquid media with nutrients, wherein a recirculation line connects the nutrient supply member and the nutrient reservoir.

16. The method of claim 10, wherein nutrients in the liquid media comprises carbohydrates.

17. The method of claim 10, further comprising, sterilizing the liquid media in a sterilization tank, connected to the nutrient reservoir, prior to delivering the liquid media to the one or more mycelium feed assemblies.

18. The method of claim 10, wherein the one or more mycelium feed assemblies are arranged within a growth chamber, wherein the growth chamber is an enclosed system to maintain a sterile environment.

19. The method of claim 18, further comprising, controlling an environment within the growth chamber by adjusting one or more growth chamber environmental controls, including temperature, humidity, light, gas compositions, and air flow.

20. The method of claim 10, wherein the nutrient supply member in each of the one or more mycelium feed assemblies has a hollow structure.

* * * * *